United States Patent
Cullinan et al.

(12) 
(10) Patent No.: US 6,258,826 B1
(45) Date of Patent: Jul. 10, 2001

(54) PHARMACEUTICAL FORMULATIONS AND APPLICATIONS THEREOF FOR THE TREATMENT OF ESTROGEN DEPRIVATION SYNDROME

(75) Inventors: George Joseph Cullinan, Trafalgar; Brian Stephen Muehl; Kenneth Jeff Thrasher, both of Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/388,340

(22) Filed: Sep. 1, 1999

Related U.S. Application Data

(60) Provisional application No. 60/104,011, filed on Oct. 13, 1998.

(51) Int. Cl.[7] .................. A61K 31/445; C07D 409/12
(52) U.S. Cl. .................. 514/324; 514/212; 514/422; 514/443; 540/536; 546/202; 548/525
(58) Field of Search .................. 514/212, 324, 514/422, 443; 540/536; 546/202; 548/525

(56) References Cited

U.S. PATENT DOCUMENTS

| | | | |
|---|---|---|---|
| 3,278,552 | * 10/1966 | Geering et al. | 549/42 |
| 4,133,814 | 1/1979 | Jones et al. | 546/202 |
| 4,418,068 | 11/1983 | Jones | 514/320 |
| 4,588,484 | 5/1986 | Justice, Jr. et al. | 204/59 R |
| 5,389,670 | 2/1995 | Fontana | 514/443 |
| 5,391,557 | 2/1995 | Cullinan et al. | 514/324 |
| 5,393,763 | 2/1995 | Black et al. | 514/333 |
| 5,464,845 | 11/1995 | Black et al. | 514/326 |
| 5,488,058 | 1/1996 | Palkowitz | 514/324 |
| 5,492,922 | 2/1996 | Palkowitz | 514/324 |
| 5,510,357 | 4/1996 | Palkowitz | 514/324 |
| 5,514,703 | 5/1996 | Carlson et al. | 514/443 |
| 5,514,704 | 5/1996 | Carlson et al. | 514/443 |
| 5,532,382 | 7/1996 | Carlson et al. | 549/57 |
| 5,534,526 | 7/1996 | Cullinan | 514/432 |
| 5,641,790 | 6/1997 | Draper | 514/333 |
| 5,646,137 | 7/1997 | Black et al. | 514/171 |
| 5,650,425 | * 7/1997 | Biegnon et al. | 514/408 |
| 5,670,514 | 9/1997 | Audia et al. | 514/298 |
| 5,686,476 | 11/1997 | May | 514/324 |
| 5,723,474 | 3/1998 | Palkowitz | 514/324 |
| 5,731,342 | 3/1998 | Cullinan et al. | 514/443 |
| 5,747,510 | 5/1998 | Draper | 514/333 |
| 5,760,061 | 6/1998 | Fontana | 514/324 |
| 5,811,120 | 9/1998 | Gibson et al. | 424/464 |
| 5,972,383 | 10/1999 | Gibson et al. | 424/464 |

FOREIGN PATENT DOCUMENTS

| | | |
|---|---|---|
| 0729 956 A1 | 2/1996 | (EP) . |
| 0747376 A1 | 5/1996 | (EP) . |
| 0 827 959 A2 | 8/1997 | (EP) . |
| WO 970 1549 A1 | 6/1996 | (WO) . |
| WO 98/45287 | 4/1998 | (WO) . |
| WO 99/25706 | 11/1998 | (WO) . |
| WO 99/25707 | 11/1998 | (WO) . |

OTHER PUBLICATIONS

Pinto et al. "Chemistry and pharmacokinetics of diarylthiophenes and . . . " CA 126:152396, 1996.*

Draper et al., "effects of Raloxifene (LY 1394841 HCI) on Biochemical Markers of Bone and Lipid Metabolism Healthy Postmemopausal Women", Hong Kong, Fourth Int'l Symp. on Osteoporosis, Mar. 29, 1993.

Bryant et al., "Protection fro Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist",Am Soc. Bone & Min. Res., Tampa, Sep. 18–22, 1993.

Frolik et al., "In Vivo and In Vitro Metabolism of Raloxifene", Am.Soc. Bone & Min. Res., Tampa Sep. 18–22, 1993.

Glasebrook et al., "Multiple Binding Sites for the Antiestrogen Raloxifene", Am Soc. Bone & Min. Res., Tampa, Sep. 18–22, 1993.

(List continued on next page.)

*Primary Examiner*—Ceila Chang
(74) *Attorney, Agent, or Firm*—William R. Boudreaux

(57) ABSTRACT

Formulations and applications thereof are described which are useful for the inhibition of various medical conditions associated with estrogen deprivation syndrome including osteoporosis and hyperlipidemia utilizing compounds of structure I represented by the following structure

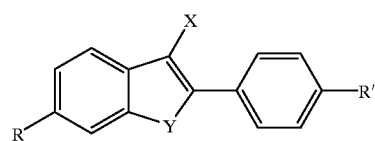

in combination with compounds of formula II represented by the following structure

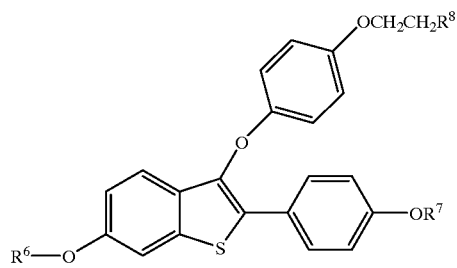

where X, Y, R, R', $R^6$, $R^7$ and $R^8$ are as defined herein.

24 Claims, No Drawings

OTHER PUBLICATIONS

Hock et al., "Combination of Raloxifene and Human Parathyoid Hormone 1–34; Increased Femur Bone Mass in Young Ovariectomized (OVX) Rats", Am. Soc Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene and Anti–Estrogen, Simulates the Effects of Estrogen in Inhibiting Bone Resorption Through Regulating TCGB–3 Expression in Bone; "Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series; "The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109; 1981, 987–989.

Black, L.J. "Biological Actions and Binding Properties of a New Estrogen Antogosist LY117018," In: Hormone Antagonists, 129–82, 1982, (M.K. Agarwal ed.) Walter de Gruyter and Co., Berlin New York.

Black, et al., LY15678: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New Benzothiophene Derived Antiestrogen, Life Sciences, 32:1983, 1031–1036.

Black et al., The Relationship of the Antiestrogenic Efficacy of LY156758 too its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22:1979, 962–966.

Black et al., Antiestrogens 2, Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med.Chem. 27(8), 1984, 1057–166.

Health News Daily, vol. 9, No. 239, p. 1—Dec. 11, 1997.

Palkowitz, et al., Discovery and Synthesis of [6–Hydroxy–3–[4–[2–(1–piperidinyl)ethoxy]phenoxy]–2–(4 hydrooxyphenyl)]benzo[b]thiophene: A Novel, Highly Potent, Selective Estrogen Receptor Modulator, J. Med. Chem., 40(10), 1407–1416 (1997).

Capozzi, et al., Phthalimidesulfenyl Chloride; Part VII: Synthesis of 2–Substituted 3–Chlorobenzo[b]thio[jemes amd Related Heteroaromatics, Synthesis, (5) 521–525 (1994).

Khovidhunkit, et al., "Clinical Effects of Raloxifene Hydrochloride in Women", Ann Intern Med, 130:431–9 (1999).

Delmas, et al., Effects of Raloxifene on Bone Mineral Density, Serum Cholesterol Concentrations, and Uterine Endometrium in Postmenopausal Women, N. Engl J. Med., 337:1641–7 (1997).

Walsh, et al., "Effects of Raloxifene on Serum Lipids and Coagulation Factors in Healthy Postmenopausal Women", JAMA 279:1445–51 (1998).

Cummings, et al., "The Effect of Raloxifene on Risk of Breast Cancer in Postmenopausal Women" JAMA, 281:2189–97 (1999).

Ettinger, et al., "Reduction of Vertebral Fracture Risk in Postmenopausal Women with Osteoporosis Treated with Raloxifene: Results from a 3–year randomized clinical trial" J. Am Med Assoc. 282:637–45 (1999).

Nickelsen, et al., "Raloxifene Hydrochloride, a Selective Estrogen Receptor Modulator: Safety Assessment of Effects on Cognitive Function and Mood in Postmenopausal Women" Psychoneuroendocrinology, 24:115–28 (1999).

* cited by examiner

PHARMACEUTICAL FORMULATIONS AND APPLICATIONS THEREOF FOR THE TREATMENT OF ESTROGEN DEPRIVATION SYNDROME

CROSS-REFERENCE

This application claims the benefit of U.S. Provisional Application No. 60/104,011, filed Oct. 13, 1998.

FIELD OF THE INVENTION

The present invention relates to pharmaceutical formulations and applications thereof for the treatment of estrogen deficiencies, in particular, formulations containing 2-aryl-3-halobenzo[b]thiophenes.

BACKGROUND OF THE INVENTION

The term "estrogen deprivation syndrome" has been used in the art to describe various pathological conditions which frequently affect women who have insufficient levels of the hormone estrogen. The most common cause of estrogen deprivation in women is the natural cessation of menses with age, i.e., menopause. Additionally, non-natural circumstances including surgical ovariectomy, chemotherapy causing the cessation of hormone production or pharmacologic action, and the like, may induce estrogen deprivation. Although numerous pathologies are contemplated by the use of this term, the greatest long-term medical concerns resulting from estrogen deprivation syndrome are osteoporosis and cardiovascular effects, especially hyperlipidemia.

Osteoporosis describes a group of diseases which arise from diverse etiologies; however, all of the diseases within the group can be characterized by the net loss of bone mass per unit volume. The consequence of this loss of bone mass is the failure of the skeleton to provide adequate structural support for the body i.e. bone fracture. One of the most common types of osteoporosis is that associated with menopause. Most women lose from about 20% to about 60% of the bone mass in the trabecular compartment of the bone within 3 to 6 years after the cessation of menses. This rapid loss is generally associated with an overall increase of the bone resorption and bone formation cycle where the resorptive cycle is more dominant. The obvious result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Although osteoporosis is not generally thought of as a life threatening condition, twenty percent (20%) to thirty percent (30%) of the mortality rate for elderly women is attributed to hip fractures. A large percentage of this mortality rate can be directly associated with post-menopausal osteoporosis.

Estrogen deficiencies has also been attributed to cardiovascular disease in women. Throughout pre-menopausal time, most women have less incidence of cardiovascular disease than age-matched men. However, following menopause, the rate of cardiovascular disease in women slowly increases to match the rate seen in men. This loss of protection has been linked to the loss of estrogen and, in particular, to the reduced ability for estrogen to regulate the levels of serum lipids. The mechanism by which estrogen regulates serum lipids is not well understood, but evidence to date indicates that estrogen can upregulate the low density lipid (LDL) receptors in the liver to remove excess cholesterol. Estrogen also appears to have some effect on the biosynthesis of cholesterol, and other beneficial effects on cardiovascular health.

In addition to the major estrogen deprivation pathologies (supra), there are many serious, but less common maladies as well as a larger number of less serious, yet significant sequela. For example, serious pathologies include: neurodegenerative diseases such as Alzheimer's disease and various autoimmune diseases such as rheumatoid arthritis, lupus erythematosus, and the like. These pathologies are more prevalent in women, particularly in post-menopausal women as opposed to pre-menopausal. Less serious conditions, such as, urinary incontinence, skin and hair quality deterioration, vaginal dryness, hot flashes, and the like, also, occur more frequently in women past menopause.

Although estrogen replacement therapy is often prescribed for the estrogen deprivation syndrome, current treatments suffer from poor patient compliance as many women object to some of the side-effects and the inconvenience of the pharmaceutical forms of the medication. For example, 17-β-estradiol is often administered via a transdermal patch because of its poor oral absorption. As a result, a majority of women cease taking estrogen within the first year of estrogen replacement therapy.

SUMMARY OF THE INVENTION

The present invention provides a pharmaceutical formulation which comprises a compound having the following structure:

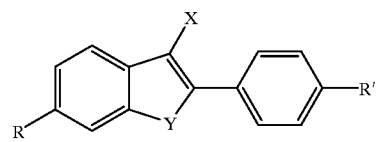

I wherein: R and R' are independently hydrogen, hydroxy, —O(C$_1$-C$_4$ alkyl), —OCH$_2$Ar, —OCO(C$_1$-C$_6$ alkyl), —OCOAr,
where Ar is phenyl or substituted phenyl; X is F, Cl, Br, or I; Y is S or S—O; and pharmaceutically acceptable solvates thereof; in combination with Compound II (depicted below).

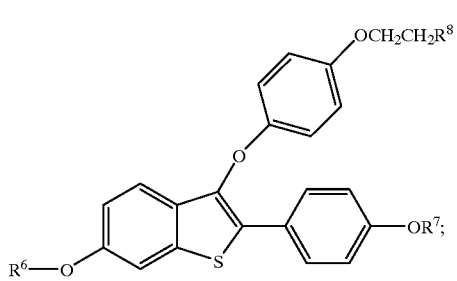

II

R$^6$ and R$^7$ are independently hydrogen, —(C$_1$-C$_4$ alkyl), —CO(C$_1$-C$_6$ alkyl), —CH$_2$Ar, or —COAr; R$^8$ is pyrolidin-1-yl, piperidin-1-yl, or hexamethyleneimin-1-yl (the nitrogen of the R$^8$ group may optionally be oxidized to the N-oxide); and pharmaceutically acceptable salts or solvates thereof.

In another embodiment of the present invention, a method is provided for inhibiting estrogen deprivation syndrome which comprises administering to a mammal (including humans) in need of such treatment, an effective amount of Compound I in combination with Compound II.

In yet another embodiment of the present invention, an article of manufacture is provided which comprises a package having deposited thereon a label describing the contents of the package and having deposited therein a pharmaceutically active material having the pharmaceutical formulation described above.

As used herein, the term "alkyl" refers to a hydrocarbon radical of the general formula $C_nH_{2n+1}$. The alkane radical may be straight, branched, cyclic, or multi-cyclic. For example, the term "$C_1$–$C_6$ alkyl" refers to monovalent, straight, branched, or cyclic aliphatic group containing 1 to 6 carbons atoms (e.g., methyl, ethyl, n-propyl, i-propyl, cyclopropyl, n-butyl, i-butyl, s-butyl, t-butyl, cyclobutyl, pentyl, neopentyl, cyclopentyl, hexyl, 2-methylpentyl, cyclohexyl, and the like). The alkane radical may be substituted or unsubstituted.

The term "halo" refers to chloride, bromide, fluoride, or iodide.

The term "substituted phenyl" refers to a phenyl group having one or more substituents attached to the aromatic ring. Preferably, the phenyl group has one to three substituents selected from the group consisting of $C_1$–$C_6$ alkyl, $C_1$–$C_4$ alkoxy, hydroxy, nitro, chloro, fluoro, or tri(chloro or fluoro)methyl.

The term "solvate" refers to an aggregate that comprises one or more molecules of the solute, such as an aggregate of compounds I or II, with one or more molecules of solvent. Suitable solvent molecules are those commonly used in the pharmaceutical art, which are known to be non-detrimental to the recipient, e.g., water and ethanol.

DETAILED DESCRIPTION

Estrogen deprivation syndrome includes those pathologies and conditions brought about by the loss of ovarian function (either natural, surgically, or chemically induced) and specifically to the loss of the ovarian hormones, especially estrogen. Since loss of estrogen is causative or contributive for the symptoms of the syndrome, administration of a pharmaceutical formulation that effects the symptoms may be useful in the treatment of estrogen deprivation syndrome. Applicants have discovered that each of the symptoms associated with estrogen loss responds to the replacement of the lost estrogen hormone through the administration of compounds having structure I (described below). Thus, formulations based on Compound I in combination with Compounds II (described below) are useful and beneficial in treating or preventing estrogen deficiency symptoms, which include but are not limited to osteoporosis, hyperlipidemia, atherosclerosis, vasomotor abnormalities (hot flashes), auto-immune diseases, skin and hair abnormalities, cardio-vascular disease and degeneration, dementia and Alzheimer's disease, depression, weight gain or loss, certain types and conditions of diabetes, inappropriate healing and tissue repair, vaginal atrophy, urinary incontinence, sequelae of abnormal regulation of estrogen controlled genes, intra alia. It should be recognized that not all patients being treated for estrogen deprivation syndrome symptoms will necessarily have all the various pathologies listed, supra, thus, the specific use of the compounds and methods of the current invention may vary depending on the idiosyncratic nature and severity of those symptoms.

Pharmaceutical formulations that include Benzo[b] thiophene compounds represented by the following structure I have been found to be useful for the treatment of estrogen deprivation syndrome.

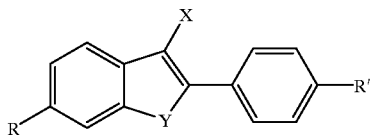

R and R' are independently hydrogen, hydroxy, —O($C_1$–$C_4$ alkyl), —OCH$_2$Ar, —OCO($C_1$–$C_6$ alkyl), —OCOAr;
Ar is phenyl or substituted phenyl; X is F, Cl, Br, or I; and Y is S or S—O; or a solvate thereof. Preferably, Y is sulfur and X is chloro or bromo. More preferably, R and R' are each hydroxy and X is chloro; or R is benzyloxy, R' is methoxy, and X is bromo.

Compounds having structure I are derivatives of benzo [b]thiophene (depicted below) which is named and numbered according to the Ring Index recommended by the American Chemical Society.

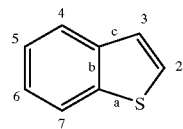

All of the compounds used in the methods and formulations of the present invention can be made according to procedures described in U.S. Pat. Nos. 4,133,814, 4,418, 068, 5,488,058, 5,510,358 and 5,731,342 (incorporated herein by reference); and in Jones, C. D., et al., *J. Med. Chem.*, 27(8), pp.1057–1066 (1984); Capozzi, G., et al., *Synthesis*, pp.521–525 (1994); Palkowitz, A. D., et al., *J. Med. Chem.*, 40(10), pp.1407–1416 (1997). The carboxylic esters of Compounds I and II may be prepared by the methods described in U.S. Pat. No. 5,393,763, incorporated herein by reference.

Compound I may be prepared by halogenation of a 3-H benzo[b]thiophene (i.e., where X is hydrogen) with a halo-Lewis acid (e.g., AlCl$_3$, BCl$_3$, and the like). Alternatively, the 3-H benzo[b]thiophene may be halogenated by treatment with elemental halogen in a solvent such as CHCl$_3$ or CCl$_4$ at ambient temperature.

Compounds having structure I may also be interconverted between various halogen classes. For example, the 3-bromo compounds may be treated with a metalating agent, such as, n-butyl lithium, a Grinard reagent, or the like. The reactions are usually carried out in anhydrous solvents such as THF, ether, benzene, and the like, at temperatures ranging from –50° to 50° C. and are generally completed in one to twenty-four hours. This procedure yields a 3-metalated-2-phenylbenzo [b]thiophene, e.g., 2-(4-methoxyphenyl)-3-lithio-6-methoxybenzo[b]thiophene (where R and R' are methoxy and X is lithium). The metalated intermediates may be treated with a source of electrophilic halogen, e.g., N-chlorosuccinimide, in an anhydrous solvent (e.g., THF, ether, toluene, etc.) at ambient temperature for sixteen hours. Hence, the 3-bromo compounds are converted to the 3-chloro compounds.

Representative examples of compounds having structure I include: 2-(4-methoxyphenyl)-3-chloro-6-methoxybenzo [b]thiophene; 2-(4-hydroxyphenyl)-3-chloro-6-hydroxybenzo[b]thiophene; 2-(4-methoxyphenyl)-3-chloro-6-hydroxybenzo[b]thiophene; 2-(4-hydroxyphenyl)-3-chloro-6-methoxybenzo[b]thiophene; 2-(4- methoxyphenyl)-3-bromo-6 -methoxybenzo[b]thiophene; 2-(4-hydroxyphenyl)-3-bromo-6-methoxybenzo[b]thiophene; 2-(4-methoxyphenyl)-3-iodo-6-hydroxybenzo[b]thiophene; 2-(4-methoxyphenyl)-3-bromo-6-benzyloxybenzo[b]thiophene; 2-(4-hydroxyphenyl)-3-bromo-6-benzyloxybenzo[b]thiophene; 2-(4-hydroxyphenyl)-3-bromo-6-hydroxybenzo[b]thiophene; 2-(4-pivaloyloxyphenyl)-3-bromo-6-pivaloyloxybenzo[b]thiophene; 2-(4-acetoxyphenyl)-3-chloro-6-acetoxybenzo[b]thiophene; 2-(4-methoxyphenyl)-3-iodo-6-methoxybenzo[b]thiophene; 2-(4-acetoxyphenyl)-3-bromo-6-methoxybenzo[b]thiophene; 2-(4-cyclopentoxyphenyl)-3-chloro-6-cyclopentoxybenzo[b]thiophene; 2-(4-methoxyphenyl)-3-bromo-6-benzyloxybenzo[b]thiophene; 2-(4-methoxyphenyl)-3-bromo-6-hydroxybenzo[b]thiophene; 2,6-dibenzyloxy-3-bromo-benzo[b]thiophene; 2-hydroxy-3-bromo-6-benzyloxybenzo[b]thiophene; 2-benzyloxy-3-bromo-6-hydroxybenzo[b]thiophene; 2-methoxy-3-bromo-6-benzyloxybenzo[b]thiophene; 2-benzyloxy-3-bromo-6-methoxybenzo[b]thiophene; and the like.

Suitable formulations and uses thereof may also include a combination of a compound(s) having structure I and a compound(s) having structure II depicted below.

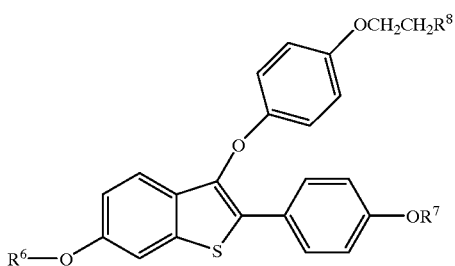

$R^6$ and $R^7$ are independently hydrogen, —($C_1$–$C_4$ alkyl), —CO($C_1$–$C_6$ alkyl), —$CH_2Ar$, or —COAr; $R^8$ is pyrolidin-1-yl, piperidin-1-yl, or hexamethyleneimin-1-yl(the nitrogen of the $R^8$ group may optionally be oxidized to the N-oxide); and pharmaceutically acceptable salts or solvates thereof.

Representative examples of compounds having structure II that may be combined with Compound I include [6-hydroxy-3-[4-[2-(1-piperidinyl)ethoxy]phenoxy]-2-(4-methoxyphenyl) benzo[b]thiophene hydrochloride; [6-hydroxy-3-[4-[2-(1-piperidinyl)ethoxy]phenoxy]-2-(4-methoxyphenyl) benzo[b]thiophene N-oxide; [6-hydroxy-3-[4-[2-(1-piperidinyl)ethoxy]phenoxy]-2-(4-hydroxyphenyl) benzo[b]thiophene hydrochloride; [6-methoxy-3-[4-[2-(1-piperidinyl)ethoxy]phenoxy]-2-(4-methoxyphenyl) benzo[b]thiophene hydrochloride; and the like. Preferably, Compound I is combined with the hydrochloride salt of [6-hydroxy-3-[4-[2-(1-piperidinyl)ethoxy]phenoxy]-2-(4-methoxyphenyl)benzo[b]thiophene ($R^6$ is hydroxy, $R^7$ is methoxy, and $R^8$ is piperidinyl).

While all the formulations and methods employing a combination of a compound I and compound II are useful, a preferred combination includes: 2-(4-methoxyphenyl)-3-bromo-6-benzyloxylbenzo[b]thiophene and [6-hydroxy-3-[4-[2-(1-piperidinyl)ethoxy]phenoxy]-2-(4-methoxyphenyl) benzo[b]thiophene hydrochloride.

Although the free-base form of Compound II can be used in the formulations and methods of the present invention, preferably, the compounds are in the form of a pharmaceutical salt. Typical pharmaceutical salts include those salts prepared by reaction of the Compound II with a mineral or organic acid. Such salts are known as acid addition salts. Thus, the term "pharmaceutically acceptable salt" refers to acid addition salts of compounds having structure II which are substantially non-toxic at the doses administered and are commonly known in the pharmaceutical literature. See e.g. Berge, S. M, et al., *J. Pharm. Sci.*, 66(1), (1977). The pharmaceutical salts generally have enhanced solubility characteristics compared to the compounds from which they are derived; consequently, the salts are often more amenable for use in pharmaceutical formulations.

Representative examples of pharmaceutical salts include hydrochloride, hydrobromide, sulfate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, g-hydroxybutyrate, b-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like of Compounds II or II. A preferred salt is the hydrochloride salt.

A typical formulation comprises an effective amount of Compound I combined with Compound II (including its pharmaceutically acceptable salt or solvate) with a pharmaceutically acceptable carrier, diluent or excipient. As used herein, the term "effective amount" refers to an amount of compound or compounds of the present invention which is capable of inhibiting or preventing the symptoms of the various pathological conditions and sequelae, herein described. The terms "inhibit" or "inhibiting" refers to prohibiting, treating, alleviating, ameliorating, halting, restraining, slowing or reversing the progression, or reducing the severity of a pathological symptom related to or resultant from estrogen deprivation syndrome. As such, these methods include both medical therapeutic (acute) and/or prophylactic (prevention) administration as appropriate.

The active ingredient is typically formulated into pharmaceutical dosage forms to provide an easily controllable dosage of the drug and to give the patient an elegant and easily handleable product. As used herein, the term "unit dose" or "unit dosage" refers to physically discrete units that contain a predetermined quantity of active ingredient calculated to produce a desired therapeutic effect. The total active ingredients is generally present from 0.1% to 99.9% by weight of the formulation.

The dosage to be administered may vary depending upon the physical characteristics of the patient, the severity of the patient's symptoms, and the means used to administer the drug. The specific dose for a given patient is usually set by the judgment of the attending physician. A typical daily dose of Compound I would contain a nontoxic dosage level of from about 0.001 mg to about 800 mg/day. Preferred daily doses generally will be from about 0.001 mg to about 60 mg/day. Such a dosage may be given as a single dose or may be divided into two or three separate doses per day as necessary.

As mentioned, supra, compounds represented by structure I may be used with a compound represented by structure II. Again, the exact amounts of the two agents (Compound I and II) may vary depending on the nature of the symptoms to be treated as well as the patient's medical status. In general, the combinations include 0.001 mg to 60 mg of Compound I and 1.0 to 60 mg of Compound II per unit dose. A preferred formulation contains 0.001 to 1 mg of Compound I and 1 to 60 mg of Compound II per unit dose, more preferred, 0.001 to 0.1 mg of Compound I and 30 to 60 mg of Compound II, in particular, 0.001 to 0.1 mg of Compound I (where R and R' are independently hydroxy or methoxy) and 30 to 60 mg of [6-hydroxy-3-[4-[2-(1-piperidinyl) ethoxy]phenoxy]-2-(4-methoxyphenyl)benzo[b]thiophene hydrochloride.

The active benzo[b]thiophene compounds can be administered by a variety of routes including oral, rectal, transdermal, buccal, aerosal, topical, opthalmic, subcutaneous, intravenous, intramuscular, intranasal, and the like. The compounds are generally formulated prior to administration, the selection of which will be decided by the attending physician.

Pharmaceutical formulations of the present invention can be prepared by procedures known in the art using well known and readily available ingredients. For example, the compounds represented by structure I, or the combination of Compounds I and II, can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The compounds can also be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

The pharmaceutical composition (or formulation) for application may be packaged in a variety of ways depending upon the method used for administering the drug. Generally, an article for distribution includes a container which contains the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label which describes the contents of the container. The label may also include appropriate warnings.

The following Examples illustrate the preparation of Compounds represented by structure I and their use in formulations and methods of the present invention. The examples are not intended to be limiting to the scope of the invention in any respect, and should not be so construed.

EXAMPLES

The terms and abbreviations used in the preparations and examples have their normal meanings unless otherwise designated.

Preparations
Preparation of 2-(4-Pivaloyloxyphenyl)-3-bromo-6-pivaloyl oxybenzo[b]thiophene (1(a)):

1.8 g (4.4 mmol) of 2-(4-Pivaloyloxyphenyl)-6-pivaloyloxybenzo[b]thiophene is dissolved in 50 mL of $CHCl_3$ and 0.23 mL (4.4 mmol) of $Br_2$ dissolved in 3 mL of $CCl_4$ is added dropwise. The reaction mixture is stirred for 30 minutes at ambient temperature and under a nitrogen atmosphere. The reaction volatiles are removed by evaporation in vacuo. The crude product is crystallized from hot EtOH yielding 1.4 g of a tan crystalline solid. PMR: Consistent with the proposed structure. MS: m/e=488 and 490 (M+). EA: Calc. for $C_{24}H_{25}BrO_4S$: C, 58.90; H, 5.15, Found: C, 58.75; H, 5.10.

The following examples serve to demonstrate the utility of the current invention and should not be considered limiting in any way. The experimental model used in this illustration is a model developed to mimic two of the major pathologies associated with human estrogen deprivation, i.e., hyperlipidemia and osteoporosis.

General Testing Procedures
Drug Recipients:
Seventy-five day old female Sprague Dawley rats (weight range of 200 g to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.20+1.70 C with a minimum relative humidity of 40%. The photoperiod in the room is 12 hours light and 12 hours dark.
Dosing Regimen Tissue Collection:
After a one week acclimation period (two weeks post-OVX) daily dosing with test compound or 17-α-ethynyl estradiol is initiated. The doses are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation-with $CO_2$, the uterus was removed through a midline incision, and a wet uterine weight was determined.
Hyperlipidemia (Cholesterol Analysis):
Blood samples are allowed to clot at ambient temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Formulations containing compounds represented by structure I reduced serum cholesterol compared to the ovariectomized control animals. For example, Compound 1(a), when tested in the assay, supra, had the following results: at 0.1 mg/kg serum cholesterol was lower 71.2% below the untreated control animals, at 1.0 and 10.0 mg/kg, the serum cholesterol was lower by 93.4 and 96.55, respectively; for reference ethynylestradiol at 0.1 mg/kg lowered cholesterol by 84.4%, all values were statistically significant at $p<0.05$.

Osteoporosis:

Following the General Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, formulations containing compounds having structure I and ethynyl estradiol ($EE_2$) in 20% hydroxypropyl β-cyclodextrin were orally administered to test animals and demonstrated a positive result, i.e., a reduction in the loss of bone mineral density.

Alzheimer's Disease:

Methods of the current invention for the treatment or prevention of Alzheimer's disease, especially in post-menopausal women, may be demonstrated by means of the following assays.

Assay 1

An animal model of neuronal damage may be used to demonstrate the methods of the current invention. For example, between twenty and thirty rats are utilized in a manner similar to that described, supra, with the difference being that a neuronal lesion is produced in the brain of the test animals. Neuronal damage, similar to the eventual damage seen in afflicted patients, can be induced with a well known technique of occluding the four vessels feeding the brain for short period of time, usually five to fifteen minutes. This occlusion causes a global ischemia which in turn causes neuronal damage. After the occlusion, the animals are allowed to rest for several days, during which time the brain lesions develop. The animals are sacrificed and damage is assessed by standard histologic techniques.

The activity of the compounds represented by structure I and structure II is illustrated by a decrease in the neuronal damage, especially, to the hippocampus and striatum.

Assay 2

Ten to fifty women are selected for a clinical study. The selection criteria are: at least one year post-menopausal, in reasonable good health, and have been diagnosed with early stages Alzheimer's Disease (AD). Further, these patients are staged in their disease, such that there is a good expectation that during the course of the study, most patients will experience a marked increase in the severity of pathologic symptoms. The patients are divided into two groups, one group is given a placebo, while the test group is given 10–100 mg of a compound of the current invention, once a day, via the oral route. The study is continued for six to thirty-six months in duration. All patients are given a complete mental profile at the beginning, each six months, and at termination of the study. This profile, used to evaluated the extent of the disease, includes capacity factors such as memory, cognition, reasoning ability, self-sufficiency, and the like. Also, included in the patient evaluation are objective parameters such as changes in brain structure as measured by CAT scanning techniques. Such methodologies and mental evaluations may be found in many standard texts on the subject. The results are compared both between groups at various time points and the changes in each patient versus time. A positive result is demonstrated by an inhibition in the type or severity of the degenerative symptoms in the test group given a formulation of the present invention, in contrast to those patients given the placebo.

In clinical use, the specific doses of Compounds I and II will, of course, be determined by the particular circumstances surrounding the case. Similarly, the route of administration is a factor determined by the specifics of each case. Thus, the exact dose and route of administration are best determined by the attending physician.

We claim:

1. A pharmaceutical formulation comprising
   (a) a compound represented by structure I

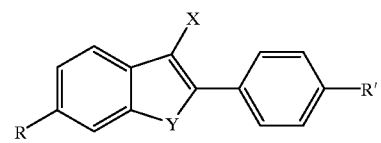

wherein
   R and R' are independently hydrogen, hydroxy, —O($C_1$–$C_4$ alkyl), —$OCH_2Ar$, —OCO($C_1$–$C_6$ alkyl), —OCOAr, where Ar is phenyl or substituted phenyl;
X is F, Cl, Br, or I;
Y is S or S-0; and
pharmaceutically acceptable solvates thereof;
   (b) a compound represented by structure II

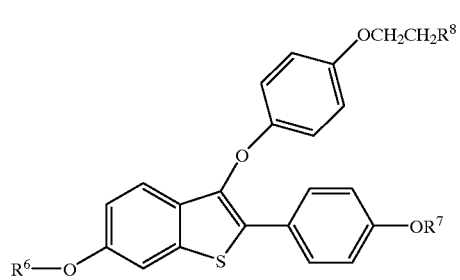

wherein:
   $R^6$ and $R^7$ are independently hydrogen, —($C_1$–$C_4$ alkyl), —CO($C_1$–$C_6$ alkyl), —$CH_2Ar$, or —COAr, where Ar is phenyl or substituted phenyl;

R⁸ is pyrolidin-1-yl, piperidin-1-yl, hexamethyleneimin-1-yl, pyrolidin-1-yl N-oxide, piperidin-1-yl N-oxide, or hexamethyleneimin-1-yl N-oxide; and pharmaceutically acceptable salts or solvates thereof; and;

(c) a pharmaceutically inert carrier.

2. The formulation of claim 1 wherein said compound represented by structure I is selected from the group consisting of 2-(4-methoxyphenyl)-3-chloro-6-methoxybenzo[b]thiophene; 2-(4-hydroxyphenyl)-3-chloro-6-hydroxybenzo[b]thiophene; 2-(4-methoxyphenyl)-3-chloro-6-hydroxybenzo[b]thiophene; 2-(4-hydroxyphenyl)-3-chloro-6-methoxybenzo[b]thiophene; 2-(4-methoxyphenyl)-3-bromo-6-methoxybenzo[b]thiophene; 2-(4-hydroxyphenyl)-3-bromo-6-methoxybenzo[b]thiophene; 2-(4-methoxyphenyl)-3-iodo-6-hydroxybenzo[b]thiophene; 2-(4-methoxyphenyl)-3-bromo-6-benzyloxybenzo[b]thiophene; 2-(4-hydroxyphenyl)-3-bromo-6-benzyloxybenzo[b]thiophene; 2-(4-hydroxyphenyl)-3-bromo-6-hydroxybenzo[b]thiophene; 2-(4-pivaloyloxyphenyl)-3-bromo-6-pivaloyloxybenzo[b]thiophene; 2-(4-acetoxyphenyl)-3-chloro-6-acetoxybenzo[b]thiophene; 2-(4-methoxyphenyl)-3-iodo-6-methoxybenzo[b]thiophene; 2-(4-acetoxyphenyl)-3-bromo-6-methoxybenzo[b]thiophene; 2-(4-cyclopentoxyphenyl)-3-chloro-6-cyclopentoxybenzo[b]thiophene; 2-(4-methoxyphenyl)-3-bromo-6-benzyloxybenzo[b]thiophene; 2-(4-methoxyphenyl)-3-bromo-6-hydroxybenzo[b]thiophene; 2,6-dibenzyloxy-3-bromo-benzo[b]thiophene; 2-hydroxy-3-bromo-6-benzyloxybenzo[b]thiophene; 2-benzyloxy-3-bromo-6-hydroxybenzo[b]thiophene; 2-methoxy-3-bromo-6-benzyloxybenzo[b]thiophene; and 2-benzyloxy-3-bromo-6-methoxybenzo[b]thiophene.

3. The formulation of claim 2 wherein said compound represented by structure II is selected from the group -consisting of [6-hydroxy-3-[4-[2-(1-piperidinyl)ethoxy]phenoxy]-2-(4-methoxyphenyl) benzo[b]thiophene hydrochloride; [6-hydroxy-3-[4-[2-(1-piperidinyl) ethoxy]phenoxy]-2-(4-methoxyphenyl) benzo[b]thiophene N-oxide; [6-hydroxy-3-[4-[2-(1-pyrolidinyl)ethoxy]phenoxy]-2-(4-hydroxyphenyl) benzo[b]thiophene hydrochloride; and [6-methoxy-3-[4-[2-(1-piperidinyl)ethoxy]phenoxy]-2-(4-hydroxyphenyl) benzo[b]thiophene hydrochloride.

4. The formulation of claim 1 wherein R⁶ is hydroxy, R⁷ is methoxy, and R⁸ is piperidinyl.

5. The formulation of claim 1 wherein said compound represented by structure I is present in amount from about 0.001 to 60 mg per unit dose and said compound represented by structure II is present in an amount from about 1.0 to 60 mg per unit dose.

6. The formulation of claim 3 wherein said compound represented by structure I is either 2-(4-methoxyphenyl)-3-bromo-6-benzyloxylbenzo[b]thiophene or 2-(4-hydroxyphenyl)-3-chloro-6-hydroxy benzo[b]thiophene.

7. The formulation of claim 6 wherein said compound represented by structure II is [6-hydroxy-3-[4-[2-(1-piperidinyl)ethoxy]phenoxy]-2-(4-methoxyphenyl) benzo[b]thiophene hydrochloride.

8. A method for inhibiting a pathology of estrogen deprivation syndrome in a mammal in need of such treatment comprising the step of administering to said mammal (a) an effective amount of a compound represented by structure I

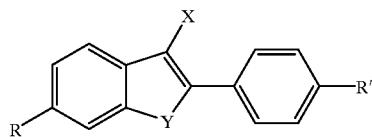

wherein:
R and R' are independently hydrogen, hydroxy, —O(C₁–C₄ alkyl), —CH₂Ar, —OCO(C₁–C₆ alkyl), —OCOAr, where Ar is phenyl or substituted phenyl;
X is F, Cl Br, or I;
Y is S or S—O; and
pharmaceutically acceptable solvates thereof; in combination with (b) a compound represented by structure II

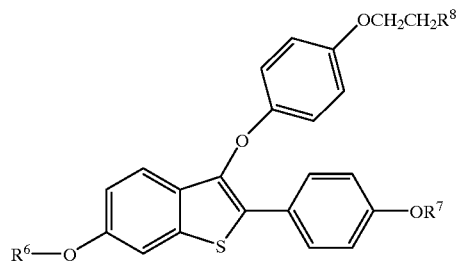

wherein:
R⁶ and R⁷ are independently hydrogen, —(C₁–C₄ alkyl), —CO(C₁–C₆ alkyl), —CH₂Ar, or —COAr, where Ar is phenyl or substituted phenyl;
R⁸ is pyrolidin-1-yl, piperidin-1-yl, or hexamethyleneimin-1-yl, pyrolidin-1-yl N-oxide, piperidin-1-yl N-oxide, or hexamethyleneimin-1-yl N-oxide; and
pharmaceutically acceptable salts or solvates thereof.

9. The method of claim 8 wherein said mammal is a female human.

10. The method of claim 9 wherein said pathology is osteoporosis.

11. The method of claim 9 wherein said pathology is hyperlipidemia.

12. The method of claim 9 wherein said pathology is Alzheimer's Disease.

13. The method of claim 9 wherein X is chloro or bromo and Y is S.

14. The method according to claim 9 wherein R and R' are hydroxy, X is chloro, and Y is S.

15. The method of claim 9 wherein X is bromo and Y is S.

16. The method of claim 9 wherein said female human is peri- or post-menopausal.

17. The method of claim 9 wherein said compound represented by structure I is selected from the group consisting of 2-(4-methoxyphenyl)-3-chloro-6-methoxybenzo[b]thiophene; 2-(4-hydroxyphenyl)-3-chloro-6-hydroxybenzo[b]thiophene; 2-(4-methoxyphenyl)-3-chloro-6-hydroxybenzo[b]thiophene; 2-(4-hydroxyphenyl)-3-chloro-6-methoxybenzo[b]thiophene; 2-(4-methoxyphenyl)-3-bromo-6-methoxybenzo[b]thiophene; 2-(4-hydroxyphenyl)-3-bromo-6-methoxybenzo[b]thiophene; 2-(4-methoxyphenyl)-3-iodo-6-hydroxybenzo[b]

thiophene; 2-(4-methoxyphenyl)-3-bromo-6-benzyloxybenzo[b]thiophene; 2-(4-hydroxyphenyl)-3-bromo-6-benzyloxybenzo[b]thiophene; 2-(4-hydroxyphenyl)-3-bromo-6-hydroxybenzo[b]thiophene; 2-(4-pivaloyloxyphenyl)-3-bromo-6-pivaloyloxybenzo[b]thiophene; 2-(4-acetoxyphenyl)-3-chloro-6-acetoxybenzo[b]thiophene; 2-(4-methoxyphenyl)-3-iodo-6-methoxybenzo[b]thiophene; 2-(4-acetoxyphenyl)-3-bromo-6-methoxybenzo[b]thiophene; 2-(4-cyclopentoxyphenyl)-3-chloro-6-cyclopentoxybenzo[b]thiophene; 2-(4-methoxyphenyl)-3-bromo-6- benzyloxybenzo[b]thiophene; 2-(4-methoxyphenyl)-3-bromo-6-hydroxybenzo[b]thiophene; 2,6-dibenzyloxy-3-bromo-benzo[b]thiophene; 2-hydroxy-3-bromo-6-benzyloxybenzo[b]thiophene; 2-benzyloxy-3-bromo-6-hydroxybenzo[b]thiophene; 2-methoxy-3-bromo-6-benzyloxybenzo[b]thiophene; 2-benzyloxy-3-bromo-6-methoxybenzo[b]thiophene; and pharmaceutically acceptable solvates thereof.

18. The method of claim 9 wherein $R^6$ is hydrogen, $R^7$ is methyl, and $R^8$ is piperidin-1-yl.

19. The method of claim 18 wherein said compound represented by structure II is a hydrochloride salt.

20. The method of claim 10 wherein said compound represented by structure I is 2-(4-methoxyphenyl)-3-bromo-6-benzyloxybenzo[b]thiophene and said compound represented by structure II is [6-hydroxy-3-[4-[2-(1-piperidinyl)ethoxy]phenoxy]-2-(4-methoxyphenyl) benzo[b]thiophene hydrochloride.

21. The method of claim 11 wherein said compound represented by structure I is 2-(4-methoxyphenyl)-3-bromo-6-benzyloxybenzo[b]thiophene and said compound represented by structure II is [6-hydroxy-3-[4-[2-(1-piperidinyl)ethoxy]phenoxy]-2-(4-methoxyphenyl) benzo[b]thiophene hydrochloride.

22. The method of claim 12 wherein said compound represented by structure I is 2-(4-methoxyphenyl)-3-bromo-6-benzyloxybenzo[b]thiophene and said compound represented by structure II compound is [6-hydroxy-3-[4-[2-(1-piperidinyl) ethoxy]phenoxy]-2-(4-methoxyphenyl) benzo[b]thiophene hydrochloride.

23. An article of manufacture comprising a container having deposited therein a pharmaceutical formulation comprising (a) a compound represented by structure I

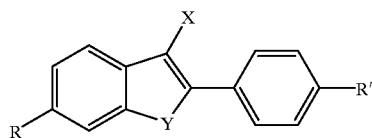

wherein
R and R' are independently hydrogen, hydroxy, —O($C_1$–$C_4$ alkyl), —OCH$_2$Ar, —OCO($C_1$–$C_6$ alkyl), —OCOAr, where Ar is phenyl or substituted phenyl;
X is F, Cl, Br, or I;
Y is S or S—O; and
pharmaceutically acceptable solvates thereof;

(b) a compound represented by structure II

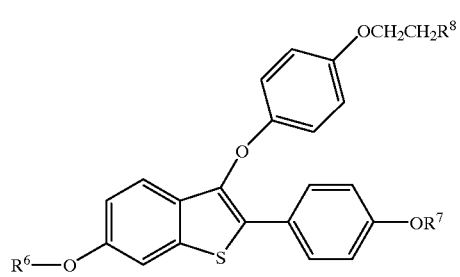

wherein:
$R^6$ and $R^7$ are independently hydrogen, —($C_1$–$C_4$ alkyl), —CO($C_1$–$C_6$ alkyl), —CH$_2$Ar, or —COAr, where Ar is phenyl or substituted phenyl;
$R^8$ is pyrolidin-1-yl, piperidin-1-yl or hexamethyleneimin-1-yl, pyrolidin-1-yl N-oxide, piperidin-1-yl N-oxide, or hexamethyleneimin-1-yl N-oxide; and
pharmaceutically acceptable salts or solvates thereof; and (c) a pharmaceutically inert carrier;
and having deposited thereon a label describing the contents of said container and use thereof for inhibiting a pathology of estrogen deprivation syndrome.

24. The article of claim 23 wherein said compound represented by structure 2 is (6-hydroxy-3-[4-[2-(1-piperidinyl)ethoxy]phenoxy]-2-(4-methoxyphenyl)benzo[b]thiophene hydrochloride.

* * * * *

UNITED STATES PATENT AND TRADEMARK OFFICE
CERTIFICATE OF CORRECTION

PATENT NO. : 6,258,826 B1
DATED : July 10, 2001
INVENTOR(S) : Cullinan, George Joseph et al.

It is certified that error appears in the above-identified patent and that said Letters Patent is hereby corrected as shown below:

Column 11,
Line 36, delete "-consisting" and insert -- consisting -- therefor.

Column 12,
Line 12, delete the word "-CH$_2$Ar," and insert -- -OCH$_2$Ar, -- therefor.

Signed and Sealed this

Thirtieth Day of April, 2002

Attest:

JAMES E. ROGAN
*Attesting Officer*     *Director of the United States Patent and Trademark Office*